United States Patent [19]

Uskokovic et al.

[11] 3,993,675

[45] Nov. 23, 1976

[54] PROCESS FOR THE PREPARATION OF 1α,25-DIHYDROXYCHOLECALCIFEROL

[75] Inventors: Milan Radoje Uskokovic, Upper Montclair; Thomas Albert Narwid, Pompton Plains, both of N.J.; Jerome Anthony Iacobelli, Woodside, N.Y.; Enrico Baggiolini, Nutley, N.J.

[73] Assignee: Hoffmann-La Roche Inc., Nutley, N.J.

[22] Filed: Feb. 24, 1975

[21] Appl. No.: 552,027

[52] U.S. Cl. .................. 260/397.2; 260/239.55 R
[51] Int. Cl.² ............................................ C07J 5/00
[58] Field of Search ................................. 260/397.2

[56] References Cited
UNITED STATES PATENTS

| | | | |
|---|---|---|---|
| 3,833,622 | 9/1974 | Babcock et al. | 260/397.2 |
| 3,887,545 | 6/1975 | Iacobelli et al. | 260/239.55 |

*Primary Examiner*—Elbert L. Roberts
*Attorney, Agent, or Firm*—Samuel L. Welt; George M. Gould; Raymond R. Wittekind

[57] ABSTRACT

A novel process for the preparation of 1α,25-dihydroxycholecalciferol and intermediates thereof is disclosed.

17 Claims, No Drawings

PROCESS FOR THE PREPARATION OF 1α,25-DIHYDROXYCHOLECALCIFEROL

BACKGROUND OF THE INVENTION

It is generally accepted that 1α,25-dihydroxycholecalciferol (1α,25-dihydroxyvitamin $D_3$), the rapid-acting, natural metabolite of vitamin $D_3$, is more active than vitamin $D_3$ for intestinal calcium transport and bone calcium mobilization. This subject is extensively reviewed by DeLuca, et al. in Physiological Reviews, 53, 327 (1973).

In 1972 DeLuca, et al. described a 21-step synthesis of non-crystalline 1α,25-dihydroxycholecalciferol starting from i-homocholanic acid in Tetrahedron Letters, 4147 (1972). In 1974 Barton et al. described an 8-step synthesis of crystalline 1α,25-dihydroxycholecalciferol starting from 1α,25-diacetoxycholesterol 3-acetate, irradiating 1α,25-diacetoxy-7-dehydrocholesterol 3-acetate to a mixture of its photoisomers, equilibrating the mixture of photoisomers and isolating the desired 1α,25-dihyroxyvitamin $D_3$ in J. C. S. Chem. Comm., 203 (1974).

Recently Iacobelli, Narwid and Uskoković described a new synthesis of 1α,25-dihydroxycholesterol and the corresponding 1,3,25-triacetate in U.S. Patent Application Ser. No. 415,186. The utilization of these cholesterol derivatives in a process for the preparation of 1α,25-dihydroxyvitamin $D_3$, overcoming the inherent difficulties of the two previously reported syntheses and thereby making this important metabolite of vitamin $D_3$ readily available for pharmacological, clinical and therapeutic use would represent a major advance in the vitamin D field.

DETAILED DESCRIPTION OF THE INVENTION

The present invention relates to a novel, efficient method for the preparation of 1α,25-dihydroxycholecalciferol starting from 1α,25-dihydroxycholesterol. More particularly, the present invention relates to a method of synthesizing 1α,25-dihydroxycalciferol comprising the steps of acylating 1α,25-dihydroxycholesterol to 1α,25-diacyloxycholesterol 3-acylate, converting 1α,25-diacyloxycholesterol 3-acylate to pure 1α,25-diacyloxy-7-dehydrocholesterol 3-acylate, selectively hydrolyzing the 3-acyloxy group of 1α,25-diacyloxy-7-dehydrocholesterol 3-acylate to 1α,25-diacyloxy-7-dehydrocholesterol, irradiating pure 1α,25-diacyloxy-7-dehydrocholesterol, isolating pure 1α,25-diacyloxyprecholecalciferol, recycling readily separable unreacted starting material and isomerizing and hydrolyzing 1α,25-diacyloxyprecholecalciferol to pure crystalline 1α,25-dihydroxycholecalciferol.

The present invention also relates, more particularly, to a method of synthesizing 1α,25-dihydroxycholecalciferol from 1α,25-dihydroxycholesterol comprising the steps of converting 1α25dihydroxycholesterol to pure 1α,25-di-(tetrahydropyran-2-yloxy)-7-dehydrocholesterol or 1α,25-di-(tetrahydrofuran-2-yloxy)-7-dehydrocholesterol, irradiating pure 1α,25-di-(tetrahydropyran-2-yloxy)-7-dehydrocholesterol or 1α,25-di-(tetrahydrofuran-2-yloxy)-7-dehydrocholesterol, isolating pure 1α,25-di-(tetrahydropyran-2-yloxy)precholecalciferol or 1α,25-di-(tetrahydropyran-2-yloxy) precholecalciferol, recycling readily separable unreacted starting material and isomerizing and cleaving 1α,25-di-(tetrahydropyran-2-yloxy) or 1α,25-di-(tetrahydrofuran-2-yloxy)precholecalciferol to pure crystalline 1α,25-dihydroxycholecalciferol.

In the formulas presented herein, the various substituents are illustrated as joined to the steroid nucleus by one of three notations: a solid line (—) indicating a substituent which is in the β-orientation (i.e., above the plane of the molecule), a dotted line (------) indicating a substituent which is in the α-orientation (i.e., below the plane of the molecule), or a wiggly line (∼) indicating a substituent which may be in the α- or β-orientation or may be a mixture of both forms. The formulas have all been drawn to show the compounds in their absolute stereochemical configurations. Since the starting materials are derived from naturally occurring materials, the final products exist in the single absolute configuration depicted herein. However, the processes of the present invention are intended to apply as well to the synthesis of steroids of the racemic series. Thus, one may begin the synthesis utilizing racemic starting materials to prepare racemic products. Optically active products can then be prepared by resolution of the racemic products utilized in the preparation thereof, as hereinafter described, by standard resolution techniques well-known in the art.

As used throughout the specification and appended claims, the term "alkyl" denotes a straight or branched chain saturated hydrocarbon radical having 1 to 8 carbon atoms; the term "cycloalkyl" denotes a cyclic saturated hydrocarbon radical having 3 to 8 carbon atoms. The term "alkylcycloalkyl" denotes a straight or branched chain saturated hydrocarbon radical monosubstituted by a cycloalkyl radical; the term "alkanoyl" denotes a radical derived by abstraction of the hydroxyl group from an alkyl carboxylic acid having 2 to 8 carbon atoms; the term "cycloalkanoyl" denotes a radical derived by abstraction of the hydroxyl group from a cycloalkyl carboxylic acid having 4 to 8 carbon atoms; the term "alkylcycloalkanoyl" denotes a radical derived by abstraction of the hydroxyl group from an alkylcycloalkyl carboxylic acid having 5 to 8 carbon atoms and the term "acyl" includes the terms "alkanoyl", "cycloalkanoyl" and "alkylcycloalkyl". The term "lower" refers to the numerical range of 1 to 8.

In the first step of the process of the present invention for the preparation of 1α,25-dihydroxycholecalciferol, 1α,25-dihydroxycholesterol of formula I,

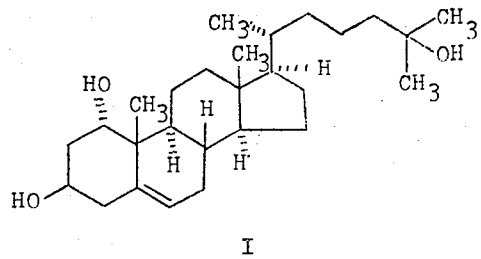

I the preparation of which is described in U.S. Patent application Ser. No. 415,186, filed Nov. 12, 1973, is converted to the triacylate of formula II

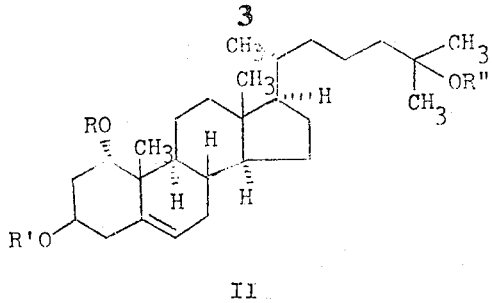

II wherein R, R' and R'' are alkanoyl having 2 to 8 carbon atoms, cycloalkanoyl having 4 to 8 carbon atoms or alkylcycloalkanoyl having 5 to 8 carbon atoms by means of acylating agents derived from straight or branched chain saturated alkane carboxylic acids having 1 to 8 carbon atoms, cycloalkane carboxylic acids having 4 to 8 carbon atoms or alkylcycloalkane carboxylic acids having 5 to 8 carbon atoms, such as alkanoyl, cycloalkanoyl and alkylcycloalkanoyl halides andd symmetrical alkanoic, cycloalkanoic and alkylcycloalkanoic anhydrides in the presence of an acid acceptor. Suitable alkanoyl, cycloalkanoyl and alkylcycloalkanoyl halides include acetyl halides, propionyl halides, 2-methylpropionyl halides, trimethylacetyl halides, hexanoyl halides, dimethylpentanoyl halides, octanoyl halides, cyclopropionyl halides, cyclopentanoyl halides, cyclohexanoyl halides, cyclopropylacetyl halides, cyclopentylacetyl halides, cyclohexylacetyl halides and so forth; acetyl chloride, hexanoyl chloride and octanoyl chloride are preferred; acetyl chloride and hexanoyl chloride are most preferred. Suitable symmetrical alkanoic anhydrides include formic anhydride, acetic anhydride, propionic anhydride, 2-methylpropionic anhydride, trimethylacetic anhydride, hexanoic anhydride, dimethylpentanoic anhydride, octanoic anhydride, cyclopropionic anhydride, cyclopentanoic anhydride, cyclohexanoic anhydride, cyclopropylacetic anhydride, cyclopentylacetic anhydride, cyclohexylacetic anhydride and the like; acetic anhydride, hexanoic anhydride and octanoic anhydride are preferred; acetic anhydride and hexanoic anhydride are most preferred. Suitable acid acceptors include alkali metal hydroxides such as, for example, sodium hydroxide and potassium hydroxide, alkali metal carbonates such as, for example, sodium carbonate and potassium carbonate, alkali metal bicarbonates such as, for example, sodium bicarbonate and potassium bicarbonate and organic tertiary amine bases, both aliphatic and heterocyclic such as, for example, triethylamine, tripropylamine, pyridine, picoline, lutidine, collidine, 1,5-diazabicyclo(5.4.0)undec-5-ene and the like. Triethylamine and pyridine are the preferred organic tertiary amine bases for the acylation of 1α,25-dihydroxycholesterol. The acylation reaction is suitably performed using an excess of from about 3 to about 150 moles of acylating agent per mole of 1α,25-dihydroxycholesterol at a temperature of from about 25° C to the boiling point of the reaction medium. When an organic tertiary amine base is used as the acid acceptor, it is advantageous to use the organic tertiary amine as the solvent medium.

Alternatively, the 3-hydroxyl group of 1α,25-dihyroxycholesterol may be selectively acylated by means of the aforementioned acylating agents in the presence of the afore-mentioned acid acceptors using an excess of from about 1 to about 7 moles of acylating agent for each mole of 1α,25-dihydroxycholesterol at a reaction temperature of from about − 10° to about 40° C, preferably about room temperature, to the monoacylate of formula II wherein R and R'' are hydrogen and R' is as hereinbefore defined.

The 3-monoacylate of 1α,25-dihydroxycholesterol is transformed to the triacylate of formula II wherein R, R' and R'' are as hereinbefore defined by the method described for the preparation of the triacylate of 1α,25-dihydroxycholesterol.

Additionally, the 1α- and 3β-hydroxyl groups of 1α,25-dihydroxycholesterol are selectively acylated by means of the afore-mentioned acylating agents in the presence of a tertiary heterocyclic amine such as, for example, pyridine, picoline, lutidine and collidine as the solvent system and acid acceptor, and N,N-dimethyl-4-aminopyridine as the catalyst at from about room temperature to about 40° C using from about 2 to 10 moles of acylating agent for each molar-equivalent of 1α,25-dihydroxycholesterol to give the 1α,3β-diacylate of formula II wherein R and R' are as hereinbefore defined and R'' is hydrogen. The diacylation is preferably performed at room temperature with about 2.5 moles of acylating agent.

The diacylate of 1α,25-dihydroxycholesterol is converted to the triacylate of formula II wherein R, R' and R'' are as hereinbefore defined by the method described for the preparation of 1α,25-dihydroxycholesterol triacylate.

In the second step of the process, 1α,25-diacyloxycholesterol-3-acylate is allylically halogenated to a mixture of 7α- and 7β-halo-1α,25-diacyloxycholesterol 3-acylates of formula III

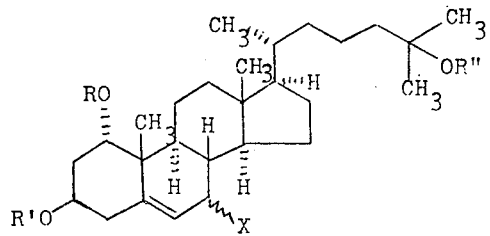

III wherein R, R' and R'' are as hereinbefore defined for formula II and X is bromo or chloro.

The halogenation of 1α,25-diacyloxycholesterol 3-acylate is accomplished using a suitable halogenating agent, such as 1,3-dibromo-5,5-dimethylhydantoin, N-chlorosuccinimide, N-chloroacetamide, N-bromosuccinimide, N-bromoacetamide and the like, dissolved in a saturated aliphatic hydrocarbon or halocarbon, such as hexane or carbon tetrachloride, in the presence of an acid scavenger, such as sodium bicarbonate or sodium carbonate at the boiling point of the reaction medium to give a mixture of the 7α- and 7β-halocholesterol acylates, which is used in the following dehydrohalogenation step without separation of the 7β-halo-isomer from the predominant 7α-isomer.

The third and one of the two crucial steps of the present process for the preparation of 1α,25-dihydroxycholecalciferol involves the dehydrohalogenation of 7ξ-halo-1α,25-diacyloxycholesterol 3-acylate to a mixture of dienes of formulas IV

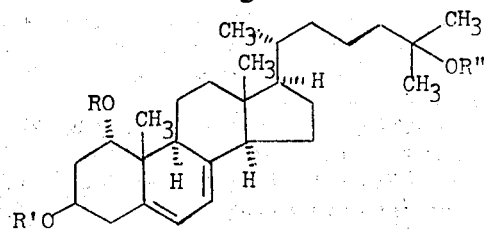

IV wherein R, R' and R'' are as hereinbefore defined and V

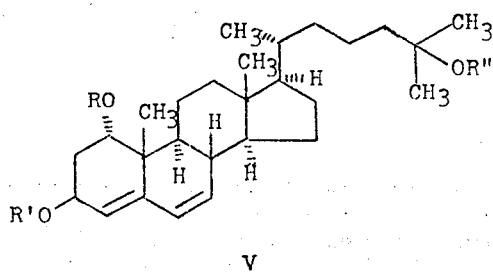

V wherein R, R' and R'' are as hereinbefore defined which are difficulty separable and which according to DeLuca et al., Tetrahedron Letters, 4147 (1950) and Barton et al., J.C.S. Chem. Comm., 203 (1974), require chromatography on silver nitrate-impregnated silica gel for isolation of the pure requisite 5,7-diene. Such chromatographic separations are costly and inefficient and, if possible, are to be avoided in a potential commercial process. It has now been found that the separation of the desired 5,7-diene of formula IV from the minor undesired isomer of formula V can be accomplished by the selective dehydroacyloxylation of the allylic 3-acyloxy group of the 4,6-diene of formula V to the 2,4,6-triene of formula VI

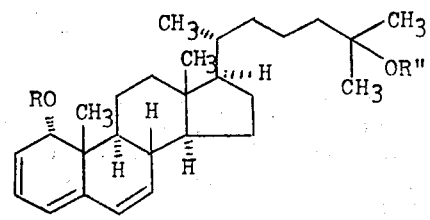

VI wherein R and R'' are as hereinbefore defined followed by either direct crystallization of the diene-triene mixture of compounds IV and VI or by filtration of the mixture through a column of a suitable absorbent followed by crystallization. Suitable absorbents for the filtration include silica gel and neutral or basic alumina. This novel process for the separation of the diene mixture does not suffer from the disadvantages of the prior art processes described by Barton, supra, and DeLuca, supra, i.e., the instant process is rapid, inexpensive, efficient, convenient and, most importantly, adaptable to large scale commercial production.

The dehydrohalogenation of the crude mixture of 7α- and 7β-halotriacyloxycholestenes is effected by heteroaromatic and aliphatic tertiary amines in an inert organic solvent. Suitable heteroaromatic tertiary amines are pyridines and alkylated pyridines, such as picolines, lutidines and collidines; suitable aliphatic tertiary amines are triethylamine, tripropylamine, 1,5-diazabicyclo(4.3.0)non-5-ene, 1,4-diazabicyclo(2.2.2)octane and the like; s-collidine being preferred. Trialkylphosphites are also useful in the dehydrohalogenation step. Suitable inert organic solvents include aromatic and aliphatic organic solvents, such as benzene, toluene, xylene, decalin and the like. Xylene is the preferred solvent. The reaction proceeds readily at temperatures from about 80° C to the reflux temperature of the reaction medium, most readily at the reflux temperature of the solvent system. The mixture of 1α,25-diacyloxy-7-dehydrocholesterol 3-acylate and 1α,25-diacyloxy-4,6-cholestadiene 3-acylate of formula IV and V respectively, so obtained, without further purification, is then dissolved in an appropriate ethereal solvent, such as dioxane, tetrahydrofuran or tetrahydropyran, dioxane being preferred, and is heated at from about 40° C to the boiling point of the reaction medium, 70° C being preferred, in the presence of a strong acid to give a mixture of 1α,25-diacyloxycholest-2,4,6-triene of formula VI wherein R and R'' are as hereinbefore defined and unchanged 1α,25-diacyloxy-7-dehydrocholestrol 3-acylate, readily separable by either direct crystallization of the crude reaction product or filtration of the crude reaction product dissolved in a suitable organic solvent system, such as methanol and chloroform, 1.25% methanol in chloroform being preferred, through a column of a suitable absorbent, such as silica gel, followed by crystallization of the concentrated eluate in excellent yield.

Appropriate strong acids include sulfuric acid and those derived from sulfuric acid, such as methanesulfonic acid, ethanesulfonic acid, hexanesulfonic acid, benzenesulfonic acid, and p-toluenesulfonic acid. Methanesulfonic acid and p-toluene sulfonic acid are the preferred acidic dehydroacylating catalysts. p-Toluenesulfonic acid is particularly preferred.

To facilitate separation of the photoisomers in the subsequent irradiation step, pure 1α,25-diacyloxy-7-dehydrocholesterol 3-acylate is selectively saponified to a mixture containing approximately 90% of a 1α,25-diacyloxy-7-dehydrocholesterol and approximately 10% of 1α-hydroxy-25-acyloxy-7-dehydrocholesterol, readily separable by filtration of a solution of the crude reaction residue and a suitable organic solvent system, such as methanol and chloroform, 1.25% methanol in chloroform being preferred, through a column of an appropriate solid absorbent, such as silica gel.

The selective saponification of 1α,25-diacyloxy-7-dehydrocholesterol 3-acylate is performed by dissolving the triacylate in a suitable solvent, cooling the solution from about −30° to about 10° C and adding dropwise over an extended period of time about an equimolar amount of a 0.5M solution of an alkali metal hydroxide, such as sodium or potassium hydroxide and a lower alkanol, such as methanol, ethanol and the like. The desired 1α,25-diacyloxycholesterol derivative is isolated by extraction with organic solvents and purified by column absorption chromatography proccedures well-known in the organic chemical art.

Suitable solvents for the selective saponification are anhydrous ethers, i.e., dioxane, tetrahydrofuran, tetrahydropyran, monoglyme, diglyme and the like, lower alkanols, such as methanol, ethanol, 2-propanol and the like, water and mixtures of lower alkanols and water.

In the next step of the process of the present invention for the preparation of 1α,25-dihydroxycholecalcifero, pure 1α,25diacyloxy-7-dehydrocholesterol dissolved in a suitable inert organic solvent system is irradiated under an inert atmosphere, such as nitrogen, helium, argon and the like, by means of a mercury lamp equipped with a glass cooling finger at a temperature range of about −40° to about +25° C, −5° C being the preferred irradiation temperature, for the period of time necessary to effect about 50% conversion of the starting material.

Suitable sources of irradiation energy include high and low pressure mercury, xenon-mercury and thallium-mercury lamps. High pressure mercury lamps are preferred. A 450W Hanovia high pressure mercury lamp is the most preferred source of irradiation energy.

The glass cooling finger may be fabricated from Vycor or Corex glass or quartz.

Suitable inert organic solvent systems for the irradiation include mixtures of saturated aliphatic hydrocarbon, such as pentane, hexane, isooctane and the like, and ethereal solvents, such as monoglyme, tetrahydrofuran, tetrahydropyran and the like.

Upon completion of the irradiation, the solvents are removed by evaporation and the residue is separated into pure 1α,25diacyloxyprecholecalciferol of formula VII

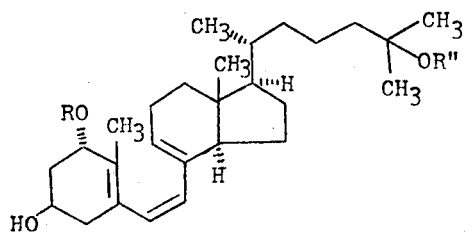

VII wherein R and R'' are as hereinbefore defined and pure unchanged 1α,25-diacyloxy-7-dehydrocholesterol of formula IV on a high pressure liquid chromatograph employing a solid absorbent column and an inert organic eluent. Suitable inert organic eluents for the separation step include mixtures of hydrocarbons, such as n-hexane, isooctane, benzene, toluene and the like and esters, such as ethyl acetate, ethyl benzoate and the like. Suitable solid absorbents include Porasil, Corasil, Biosil, Zorbax, Zorbax-Sil, Sil-X and the like. A Waters Associates Chromatograph Model 202 using an 8-ft by ⅜ inch Porasil A column and mixture of n-hexane/ethyl acetate as the eluent is the preferred high pressure liquid chromatographic system.

Unchanged 1α,25-diacyloxy-7-dehydrocholesterol is recycled through the irradiation process to obtain additional quantities of pure 1α,25 -diacyloxyprecholecalciferol, thereby rendering this crucial step of the process and the overall process highly efficient in comparison with the processes previously disclosed by Barton, supra and DeLuca, supra.

In the final step of the process for the preparation of 1α,25-dihydroxycholecalciferol of this invention, 1α,25-diacyloxyprecholecalciferol is hydrolyzed to 1α,25-dihydroxyprecholecalciferol of formula VIII

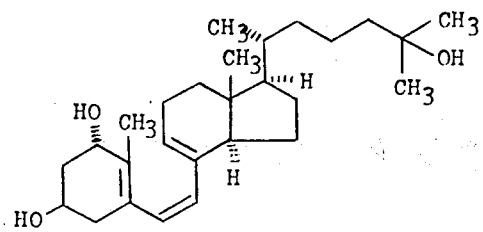

VIII by means of an alkali metal hydroxide, such as sodium or potassium hydroxide dissolved in a suitable lower alkanol, such as methanol or ethanol or the like, by procedures well-known in the art. 1α,25-Dihydroxyprecholecalciferol is then isomerized to 1α,25-cholecalciferol of formula IX

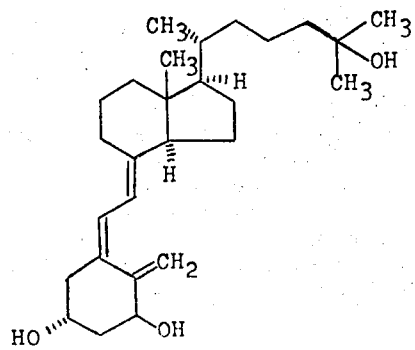

IX by heating the previtamin in an inert organic solvent, such as dioxane, tetrahydrofuran, monoglyme, diglyme and the like, under an inert atmosphere, such as argon, nitrogen, helium or the like, by methods also well-known in the art.

Alternatively, 1α,25-dihydroxycholecalciferol is prepared by irradiating 1α,25-di-(tetrahydropyran-2-yloxy)-7-dehydrocholesterol of formula IV wherein R' is hydrogen and R and R'' are tetrahydropyran-2-yl or 1α,25-di-(tetrahydrofuran-2-yloxy)-7-dehydrocholesterol of formula IV wherein R' is hydrogen and R and R'' are tetrahydrofuran-2-yl by the method described for the conversion of the corresponding acyloxy compounds of formula IV followed by cleavage of the tetrahydropyran-2-yl or tetrahydrofuran-2-yl groups and isomerization of 1α,25-dihydroxyprecholecalciferol to 1α,25-dihydroxycholecalciferol.

The cleavage reaction, i.e., the cleavage of 1α,25-di-(tetrahydropyran-2-yloxy)- and 1α,25-di-(tetrahydrofuran-2-yloxy)-precholecalciferol of formula VII wherein R and R'' are tetrahydropyrane-2-yl and tetrahydrofuran-2-yl, respectively, is effected by standard methods well-known in the art involving, for example, treatment of the tetrahydropyran- and tetrahydrofuran-2-yloxy previtamin derivatives with aqueous acidic reagents, such as hydrochloric acid, aqueous acetic acid and the like, or large excesses of alkanols, such as methanol or ethanol, in the presence of an acid-catalyst, such as p-toluenesulfonic acid, or the like, under equilibrium conditions.

1α,25-Di-(tetrahydropyran-2-yloxy)- and 1α,25-di-(tetrahydrofuran-2-yloxy)-7-dehydrocholesterol are prepared by etherification of 1α,25-dihydroxycholesterol 3-acylate with dihydropyran or dihydrofuran followed by halogenation, dehydrohalogenation and saponification of the 1α,25-di-(tetrahydropyran-2-yloxy)- and 1α,25-di-(tetrahydrofuran-2-yloxy)-7-dehydrocholesterol 3-acylates of formula IV wherein R and R'' are tetrahydropyran-2-yl or tetrahydrofuran-2-yl and R' is alkanoyl having 1 to 8 carbon atoms, cycloalkanoyl having 3 to 8 carbon atoms, and alkylcycloalkanoyl having 4 to 8 carbon atoms.

The subsequent halogenation, dehydrohalogenation and saponification steps, including the chemical and physical separation, are performed according to the procedures utilized for the corresponding transformation in the triacylate series.

The etherification of 1α,25-dihydroxycholesterol 3-acylate is performed by treatment with dihydropyran or dihydrofuran in the presence of a suitable acid-catalyst, such as p-toluenesulfonic acid, methanesulfonic acid, benzenesulfonic acid, boron trifluoride etherate, hydrochloric acid or the like, using the ethereal reactant as the solvent, at a temperaure between about room temperature and the boiling point of the reaction medium. p-Toluenesulfonic acid is the preferred acid-catalyst and room temperature the preferred reaction temperature.

The compounds of the present invention are useful as intermediates for the preparation of 1α,25-dihydroxycholecalciferol.

EXAMPLES

The following examples are illustrative only of the invention and are not to be construed as limiting the invention in any manner.

EXAMPLE 1

1α,25-Diacetoxycholesterol-3-acetate (II, R, R' and R'' are acetyl).

A solution of 1α,25-dihydroxycholesterol (I) (9.40 g, 22.5 mmoles), acetic anhydride (50 mmoles) and anhydrous pyridine (72 ml) was heated at 100° C for 17 hours with stirring. The reaction mixture was allowed to cool to room temperature and was diluted with ethyl acetate (500 ml). The solution was washed with water (2 × 100 ml), 6N hydrochloric acid (100 ml), 1N hydrochloric acid (3 × 50 ml), water (100 ml), 10% sodium bicarbonate solution (5 × 100 ml) and saturated sodium chloride solution (100 ml). Each aqueous phase was then extracted with ethyl acetate (100 ml). The combined organic extracts were dried over anhydrous sodium sulfate, filtered, and concentrated under reduced pressure to give 13.2 g of crude reaction product. The crude product was absorbed on a column (2 × 20 inches of silica gel) (500 g) and the column was eluted with 9:1 benzene/ethyl acetate (40 ml fractions) to give a 96% yield of 1α,25-diacetoxycholesterol-3-acetate as an oil.

NMR (CDCl$_3$) δ 5.50 (m, 1H, —C=C$\underline{H}$—), 5.17–4.53 (m, 2H, 2 × —C$\underline{H}$OAc), 2.03, 2.00, 1.94 (3s, 9H, 3 × C$\underline{H}_3$CO$_2$—), 1.40 (s, 6H, -CH(C$\underline{H}_3$)$_2$, 1.07 (s, 3H, C-19), 0.72 (d, 3H, J = Hz, —CHC$\underline{H}_3$), 0.67 (s, 3H, C-18).

EXAMPLE 2

1α,25-Dihydroxycholesterol-3-acetate (II, R and R'' are hydrogen, R' is acetyl).

To a solution of 1α,25-dihydroxycholesterol (I, 0.15 g, 0.36 mmoles) in anhydrous pyridine (0.8 ml), was added acetic anhydride (0.2 ml) with stirring at room temperature. After stirring for 1 hour at room temperature, the reaction mixture was poured into water (20 ml) and extracted with chloroform (5 × 20 ml). The combined organic extracts were washed with 2N sulfuric acid (25 ml), 10% sodium bicarbonate solution (25 ml) and water (25 ml), and dried over anhydrous sodium sulfate. The drying agent was removed by filtration and the filtrate was concentrated under reduced pressure to give 0.161 g of residual product. The crude product was chromatographed on a column of silica gel 60 (16 g) and the column was eluted with 1:2 ethyl acetate/dichloromethane to give 0.98 g (59%) of the monoacetate as a foam. [α]$_D^{25}$ −39.9 (CHCl$_3$), c 1.000); IR (CHCl$_3$) 3620 cm$^{-1}$ (—OH), 3490 (—OH), 1735 (—OAc); NMR (CDCl$_3$) δ 5.59 (m, 1H, —C = C$\underline{H}$—), 5.00 (m, 1H, —C$\underline{H}$OAc), 3.80 (m, 1H, —C$\underline{H}$OH), 1.97 (s, 3H, —OCOC$\underline{H}_3$), 1.17 [s, 6H, —COH(C$\underline{H}_3$)$_2$], 1.00 (s, 3H, C-19), 0.90 (d, 3H, J = 5 Hz, C-21), 0.66 (s, 3H, C-18).

EXAMPLE 3

1α-Acetoxy-25-hydroxycholesterol-3-acetate (II, R and R' are acetyl, R'' is hydrogen).

To a solution of 1α,25-dihydroxycholesterol (I, 1.04 g, 2.5 mmoles) and anhydrous pyridine (8 ml), acetic anhydride (0.561 g, 5.5 mmoles) and N,N-dimethyl-4-aminopyridine (0.050 g, 0.4 mmoles) were added at room temperature with stirring. The reaction mixture was stirred at room temperature for 5 hours and was diluted with ethyl acetate (50 ml). The resultant solution was washed with 1N hydrochloric acid (5 × 20 ml), 10% bicarbonate solution (2 × 20 ml), water (50 ml) and saturated sodium chloride solution (50 ml). The organic phase was dried over anhydrous sodium sulfate and filtered. Concentration of the filtrate under reduced pressure gave 1.20 g (96%) of the diacetate as a gum.

NMR (CDCl$_3$) δ 5.5 (m, 1H, -C=C$\underline{H}$-), 5.2–4.6 (broad, 2H, 2x —C$\underline{H}$OAc), 2.02 and 2.2 (2s, 6H, 2x —OCOC$\underline{H}_3$), 1.20 [s, 6H, —COH(C$\underline{H}_3$)$_2$], 1.09 (s, 3H, C-19), 0.92 (d, 3H, J = 5 Hz), 0.67 (s, 3H, C-18).

EXAMPLE 4

7ξ-Bromo-1α,25-diacetoxycholesterol-3-acetate (III, R, R' and R'' are acetyl and X is bromo).

A solution of 1α,25-diacetoxycholesterol-3-acetate (II, R, R' and R'' are acetyl, 11.75 g, 21.6 mmoles), dry hexane (225 ml), solid sodium bicarbonate (12.0 g) and 1,3-dibromo-5,5-dimethylhydantoin (3.5 g, 12.3 mmoles) was boiled for 20 minutes. The reaction mixture was allowed to cool to room temperature and the precipitate was collected on a filter. Evaporation of the filtrate under reduced pressure furnished 13.5 g of 7ξ-bromo-1α,25-diacetoxycholesterol-3-acetate.

EXAMPLE 5

1α,25-Diacetoxy-7-dehydrocholesterol-3-acetate (IV, R, R' and R'' are acetyl).

A solution of 7ξ-bromo-1α,25-diacetoxycholesterol-3-acetate (III, R, R', and R'' are acetyl and X is bromo, 13.5 g) in dry xylene (75 ml) was added dropwise over a 5-minute period to a solution of s-collidine (5.5 g) and dry xylene (125 ml) at room temperature. The reaction mixture was heated under reflux under an atmosphere of nitrogen for 90 minutes. At the end of this time, the reaction mixture was allowed to cool to room temperature and was diluted with benzene (500 ml). The resultant solution was washed with 1N hydrochloric acid (3 × 50 ml), water (100 ml), 10% sodium bicarbonate solution (100 ml) and water (100 ml). The organic phase was dried over anhydrous sodium sulfate and filtered. Evaporation of the filtrate under reduced pressure gave 13.2 g of a mixture of 1α,25-diacetoxy-7-dehydrocholesterol-3-acetate. (IV, R, R' and R'' are acetyl) and 1α,25-diacetoxy-4,6-cholestadiene-3-acetate (V, R, R' and R'' are acetyl). The mixture of dienes was dissolved in 250 ml of dioxane (distilled from sodium) and 1.3 g of p-toluenesulfonic acid was added. The reaction mixture was heated at 70° C for 0.5 hours under an atmosphere of nitrogen, and at the end of this time, was allowed to cool to room temperature. The reaction mixture was diluted with water (800 ml) and extracted with ethyl acetate (3 × 300 ml). Each organic extract was washed with 10% sodium bicarbonate solution (100 ml) and saturated sodium chloride solution (100 ml). The combined organic extracts were dried over anhydrous sodium sulfate and the drying agent was collected on a filter. Evaporation of the filtrate under reduced pressure gave 12.3 g of crude reaction product. The crude product was placed on a column (2¾ × 24) of Merck silica gel 60 (1 kg), and the column was eluted with 50% ethyl acetate-benzene (6.2 l) to afford 7.8 g (63.8% yield based on 1α,25-dihydroxycholesterol, I) of pure 1α,25-diacetoxy-7-dehydrocholesterol-3-acetate as a gum.

$[\alpha]_D^{25}$ —34.24° (c 0.3797, CHCl$_3$); NMR (CDCl$_3$) δ 5.66

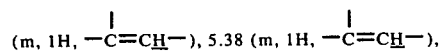
(m, 1H, —C=CH—), 5.38 (m, 1H, —C=CH—), 4.98(m, 2H, —CH—OAc), 2.06, 2.01, 1.94

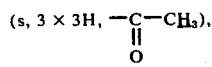
(s, 3 × 3H, —C—CH$_3$), 1.40 [s, 6H, -COAc(CH$_3$)$_2$], 1.0 (s, 3H, C-19), 0.92 (d, 3H, J = 6 Hz, —CHCH$_3$), 0.61 (s, 3H, C-18); ir (CHCl$_3$) 1725 cm$^{-1}$

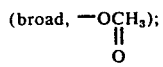
(broad, —OCH$_3$);

uv (EtOH) λ$_{max}$ 262nm (ε7000), 272 (9780), 282 (10,500), 293 (6350); mass spec. molecular ion m/e 542.

EXAMPLE 6

1α,25-Diacetoxy-7-dehydrocholesterol (IV, R and R'' are acetyl and R' is hydrogen).

A solution of 1α,25-diacetoxy-7-dehydrocholesterol-3-acetate (IV, R, R' and R'' are acetyl, 7.8 g, 14.4 mmoles) and anhydrous tetrahydrofuran (100 ml), cooled to —15° C, was added dropwise over 5 hours to a 0.574 molar solution of potassium hydroxide in methanol (12 ml). The reaction mixture was poured into water (400 ml) and extracted with ethyl acetate (4 × 200 ml). The combined organic extracts were washed with saturated sodium chlorine solution (400 ml), dried over anhydrous sodium sulfate, filtered and evaporated to give 7.2 g of crude product. The crude product was placed on a column of silica gel 60 (750 g) and the column was eluted with 1.25% methanol-chloroform (2850 ml) to give 6.0 g of the diacetate which upon recrystallization from hexane-ether afforded three crops of the pure diacetate (4.67 g, 65%), mp 133.5°–135° C.

$[\alpha]_D^{25}$ —40° (c, 0.717, CHCl$_3$): MNR (CDCl$_3$) δ 5.66 and 5.37 (multiplets, 2H, —CH=CH—), 4.95 (m, 1H, —CHOAc), 3.90 (m, 1H, HO—CH—), 2.02 (s, 3H, —OCOCH$_3$), 1.92 (s, 3H, —OCOCH$_3$), 1.38 [s, 6H, —CH(CH$_3$)$_2$], 0.97 (s, 3H, C-19), 0.91

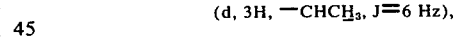
(d, 3H, —CHCH$_3$, J=6 Hz), 0.59 (s, 3H, C-18); ir (CHCl$_3$) 3580 (OH), 1725 (shoulder) and 1720 cm$^{-1}$

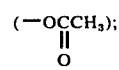
(—OCCH$_3$);

uv (EtOH) λ$_{max}$ 269nm (ε10,800), 279 (11,760), 291 (7000); mass spec. molecular ion m/e 542.

Further elution with 95:5 chloroform-methanol (1500 ml) afforded 1.06 g (15%) of 1α-hydroxy-25-acetoxy-7-dehydrocholesterol (IV, R and R' are hydrogen and R'' is acetyl).

NMR (CDCl$_3$) δ 5.7 (m, 1H, =CH—), 5.33 (m, 1H, =CH—), 4.35–3.6 (broad, 2H, 2x —CHOH), 1.94 (s, 3H, CH$_3$COO—), 1.42 [s, 6H, —COH(CH$_3$)$_2$].

EXAMPLE 7

1α,25-Diacetoxyprecholecalciferol (VII, R and R'' are acetyl). A solution of 3β-hydroxy-1α,25-diacetoxy-5,7-cholestadiene (IV, R and R'' are acetyl and R' is hydrogen, 0.500 g, 1.00 mmoles), n-hexane (80 ml) and tetrahydrofuran (20 ml) was irradiated for 13 minutes at −5° C under argon using a 450W Hanovia high pressure mercury lamp cooled with a Vycor-glass cooling finger. The solvent was removed by evaporation at 25° C under reduced pressure and the residue was purified with a Waters Associates liquid chromatograph model 202 using a 8 foot × ⅜ inch Porasil A column and a 3:1.2 mixture of n-hexane/ethyl acetate as the eluent to give 0.121 g of unchanged starting material, 3β-hydroxy-1α,25-diacetoxy-5,7-cholestadiene, and 0.096 g (25.5% conversion) of pure 1α,25-diacetoxyprecholecalciferol as a viscous oil.

NMR (CDCl$_3$) δ 5.87 (bs. 1H, -C=C$\underline{H}$-), 5.46 (m, 2H, -$\underline{H}$C=C$\underline{H}$-), 2.06, 1.96

$$(s, 2 \times 3H, -\underset{\underset{O}{\|}}{C}-C\underline{H}_3),$$

1.63 (bs, 3H, CH$_3$-19), 1.43 [s, 6H, —COAc(CH$_3$)$_2$], 0.97 (d, 3H, J = 6 Hz, —CH—C$\underline{H}_3$), 0.70 (s, 3H, C$\underline{H}_3$-18).

EXAMPLE 8

1α,25-Dihydroxyprecholecalciferol (VIII).

A solution of 1α,25-diacetoxyprecholecalciferol (VII, R and R'' are acetyl, 0.712 g, 1.42 mmoles), potassium hydroxide (2.0 g, 35.6 mmoles) and methanol (40 ml) was stirred at room temperature under argon for 30 hours. The reaction mixture was concentrated under reduced pressure. Water (50 ml) was added to the residue and the mixture was extracted with methylene chloride (3 × 100 ml). The combined organic extracts were washed with saturated sodium chloride solution (3 × 50 ml), dried over anhydrous sodium sulfate, filtered and evaporated under reduced pressure to give 0.619 g of 1α,25-dihydroxyprecholecalciferol as a thick oil.

EXAMPLE 9

1α,25-Dihydroxycholecalciferol (IX).

A solution of 1α,25-dihydroxyprecholecalciferol (VIII, 0.619 g in dioxane (30 ml) was heated under reflux for 30 minutes under an atmosphere of argon. The reaction mixture was concentrated under reduced pressure and the residue was purified with a Waters Associates liquid chromatograph model 202 using a 8 foot × ⅜ inch Porasil A column and a 5:1 mixture of ethyl acetate-n-hexane as the eluent to give 0.474 g (80% yield based on 1α,25-diacetoxyprecholecalciferol) of pure 1α,25-dihydroxycholecalciferol. Recrystallization from methyl formate afforded 0.340 g of 1α,25-dihydroxycholecalciferol as colorless crystal, mp 113°–114° C.

[α]$_D^{25}$ +47.9 (c 0.5, C$_2$H$_5$OH).

Anal. Calcd. for C$_{27}$H$_{44}$O$_3$ (MW 416.65): C, 77.84; H, 10.65; Found: C, 77.80: H, 10.72

We claim:
1. A compound of the formula

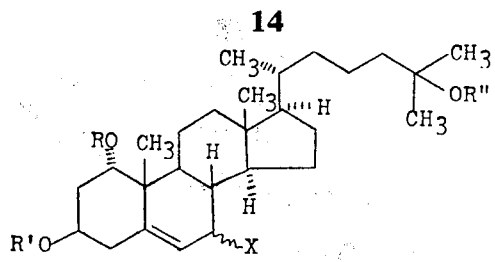

wherein R, R' and R'' are hydrogen, alkanoyl having 2 to 8 carbons atoms, cycloalkanoyl having 4 to 8 carbon atoms, alkylcycloalkanoyl having 5 to 8 carbon atoms, tetrahydropyranyl or tetrahydrofuryl and X is halo, with the proviso that R, R' and R'' are not each simultaneously acetyl when X is bromo.

2. A compound of the formula

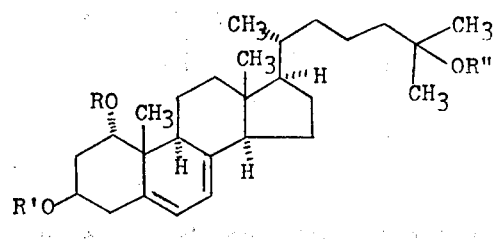

wherein R, R' and R'' are hydrogen, alkanoyl having 2 to 8 carbon atoms, cycloalkanoyl having 4 to 8 carbon atoms, alkylcycloalkanoyl having 5 to 8 carbon atoms, tetrahydropyranyl or tetrahydrofuryl, with the proviso that R, R' and R'' are not each simultaneously hydrogen or acetyl.

3. The compound according to claim 2 which is 1α,25-diacetoxy-7-dehydrocholesterol.

4. The compound according to claim 2 which is 1α-hydroxy-25-acetoxy-7-dehydrocholesterol.

5. A compound of the formula

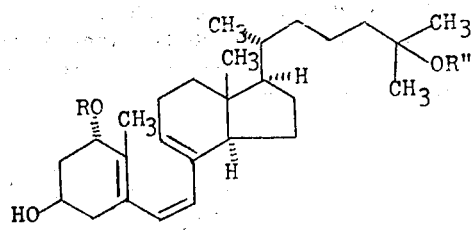

wherein R and R'' are hydrogen, alkanoyl having 2 to 8 carbon atoms, cycloalkanoyl having 4 to 8 carbon atoms, alkylcycloalkanoyl having 5 to 8 carbon atoms, tetrahydropyranyl or tetrahydrofuryl, with the proviso that R and R'' are not each simultaneously hydrogen.

6. The compound according to claim 5 which is 1α,25-diacetoxyprecholecalciferol.

7. A process for the preparation of a steroidal diene of the formula

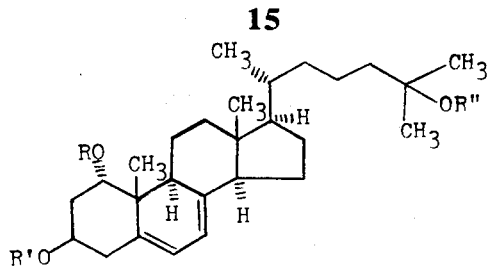

wherein R, R' and R'' are hydrogen, alkanoyl having 2 to 8 carbon atoms, cycloalkanoyl having 4 to 8 carbon atoms, alkylcycloalkanoyl having 5 to 8 carbon atoms, tetrahydropyranyl or tetrahydrofuryl which comprises a. treating a compound of the formula

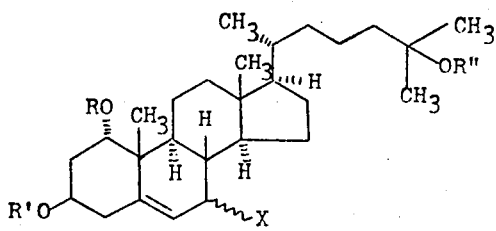

wherein R, R' and R'' are as above and X is bromo or chloro with an organic base in an inert organic solvent to form a mixture of the steroidal diene and a compound of the formula

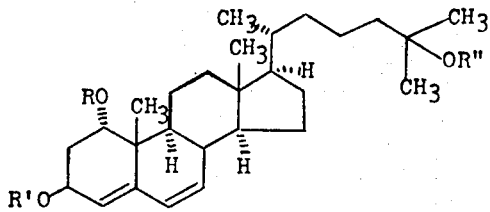

wherein R, R' and R'' are as above;
b. treating the mixture with an organic acid in a second inert organic solvent to form a second mixture of the steroidal diene

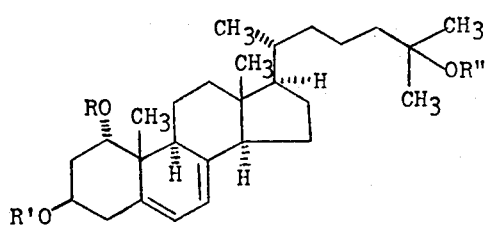

wherein R, R' and R'' are as above,
and a compound of the formula

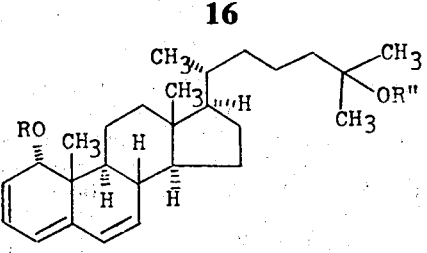

wherein R and R'' are as above; and c. separating the mixture to obtain the pure steroidal diene.

8. The process of claim 7 wherein the organic base is a heteroaromatic base.

9. The process of claim 8 wherein the heteroaromatic base is an alkylpyridine.

10. The process of claim 9 wherein the alkylpyridine is s-collidine.

11. The process of claim 7 wherein the inert organic solvet is an aromatic solvent.

12. The process of claim 11 wherein the aromatic solvent is xylene.

13. The process of claim 7 wherein R, R' and R'' are acetyl and X is bromo.

14. A process for the preparation of a compound of the formula

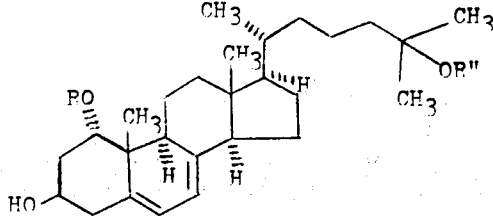

wherein R and R'' are alkanoyl having 2 to 8 carbon atoms, cycloalkanoyl having 4 to 8 carbon atoms or alkylcycloalkanoyl having 5 to 8 carbon atoms, which comprises treating a compound of the formula

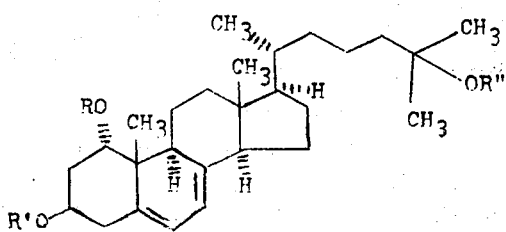

wherein R and R'' are as above and R' is alkanoyl having 2 to 8 carbon atoms, cycloalkanoyl having 4 to 8 carbon atoms or alkylcycloalkanoyl having 5 to 8 carbon atoms
with an alkali metal hydroxide in a lower alkanol at a temperature of about $-15°$ C.

15. The process according to claim 14 wherein the alkali metal hydroxide is potassium hydroxide.

16. The process according to claim 14 wherein the lower alkanol is methanol.

17. The process according to claim 14 wherein R, R' and R'' are acetyl.

* * * * *